United States Patent [19]

Härle

[11] 4,297,993
[45] Nov. 3, 1981

[54] AID FOR OSTEOSYNTHESIS

[75] Inventor: Anton Härle, Münster, Fed. Rep. of Germany

[73] Assignee: Howmedica International, Inc.-Zweigniederlassung, Kiel, Kiel, Fed. Rep. of Germany

[21] Appl. No.: 11,850

[22] Filed: Feb. 13, 1979

[30] Foreign Application Priority Data

Feb. 16, 1978 [DE] Fed. Rep. of Germany ....... 2806609

[51] Int. Cl.³ .......................... A61F 5/04; A61B 17/18
[52] U.S. Cl. ................................. 128/92 D; 128/92 G
[58] Field of Search ................ 128/92 R, 92 B, 92 C, 128/130, 260, 92 D, 92 G

[56] References Cited

U.S. PATENT DOCUMENTS

| | | | |
|---|---|---|---|
| 3,623,164 | 6/1971 | Bokros | 128/92 B |
| 3,993,073 | 11/1976 | Zaffaroni | 128/260 |
| 4,011,602 | 3/1977 | Rybicki et al. | 128/92 C |
| 4,056,496 | 11/1977 | Mancini et al. | 128/130 |
| 4,093,576 | 6/1978 | de Wijn | 128/92 C |
| 4,119,091 | 10/1978 | Partridge | 128/92 B |
| 4,155,991 | 8/1979 | Schopflin et al. | 128/130 |

Primary Examiner—Robert W. Michell
Assistant Examiner—C. W. Shedd
Attorney, Agent, or Firm—Andrus, Sceales, Starke & Sawall

[57] ABSTRACT

An aid for osteosynthesis has a bone plate containing a plurality of bores for receiving a carrier material containing an antibiotic. Grooves along the center and sides of the plate may also receive antibiotic carrier material. The outside of the carrier material may be roughened to improve fixation of the bone or tissue. Carrier material free areas may be provided on the plate to permit bending. These may be subsequently covered by caps.

9 Claims, 6 Drawing Figures

AID FOR OSTEOSYNTHESIS

The invention relates to an aid for osteosynthesis, such as a plate, nail or screw, made of a material having appropriate strength.

BACKGROUND OF THE PRESENT INVENTION

Such aids for osteosynthesis, especially metallic aids, serve for the inner fixation of a fracture. In the case of such completely covered or incompletely covered osteosyntheses, disinfection is a particular problem, since the aim must be to bring the antibiotics as far as possible directly to the site of infection.

A carrier substance provided with an antibiotic, specifically a poly-(methyl methacrylate) to which gentamycin has been added as the antibiotic, has been disclosed in a publication ("Gentamycin-PMMA-Kette", "Gentamycin-PMMA-Kugeln" ("Gentamycin-PMMA Chain", "Gentamycin-PMMA Spheres") from E. Merck, Darmstadt 1977); this carrier material ensures protracted release of the antibacterial active ingredient in reliable bactericidal concentration and ensures that despite release of the antibiotic taking place the external shape of the carrier material is retained.

This known carrier material for the antibiotic has been employed, for example, in the case of bone infections, specifically by introducing spheres, drawn up on a surgical wire, into the bone marrow cavity. The occurrence of bone infections interferes in a significant percentage (3–15%) of cases in conservative or operative treatment of open and closed fractures of the limbs. Not only is the osseous fracture consolidation hindered or greatly retarded as a result of this, but, frequently, local destruction of the bones is also associated therewith and this can give rise to frequent operations. In addition to the long treatment period, cosmetically unattractive changes in the skin and disturbances in the normal body proportions can usually not be avoided and in individual cases this disturbance of health can necessitate an amputation. The combination of conventional aids for osteosynthesis with gentamycin-PMMA chains inserted at the same time does not permit an adequately high concentration of active ingredient at the point of contact between metal and bone. On the other hand, the space requirements of the aid for osteosynthesis are in themselves already a great problem when covering, for example, an arm or lower leg with soft tissue. The additional insertion of chains would signify a considerable circulatory disturbance in the bone nourished by the periosteum and would hardly permit the necessary covering of the aid for osteosynthesis with soft tissue. Moreover, the removal of these additional chains involves a complicated and difficult operation.

In German Offenlegungsschrift No. 2,305,442, an implant for fixing inside long bones is described and it is said that cements and plastics should be avoided as fixing material in the bone.

In the literature cited above it is proposed that a pharmaceutical depot be installed at a suitable point in the implant, so that, after the operation, inflammation due to pathogens can be effectively suppressed. In the said literature it is not indicated how this pharmaceutical depot should be made up, so that it can be assumed that the inventor makes use of the teaching according to German Offenlegungsschrift No. 2 154 272, in which such a depot of pharmaceuticals by incorporation in gelatine is proposed.

SUMMARY OF THE PRESENT INVENTION

In contrast to the above, the object on which the invention is based is to provide an aid for osteosynthesis which at the same time is used as a carrier for a long-acting antibiotic, there being no change in the surface of this aid even after a prolonged period.

This object, on which the invention is based, is achieved by the application of antibiotics uniformly distributed in a non-reabsorbable carrier material of a constant surface form on the surface of the aid for osteosynthesis.

Thus, by this means an aid is provided which, whilst having the same strength as the aids of the prior art, now additionally has the advantage that when the aid itself is fitted the antibiotic is at the same time introduced into the wound area and that when the aid is removed the carrier material is removed again. Growing of endogenous tissue into the aid is excluded due to the constant surface and the non-reabsorbable property of the carrier material.

The carrier material including the antibiotic distributed therein can be completely or partially coated onto the surface of the aid. An alternative embodiment is characterized by receiving spaces which are open to the outside of the aid which serve to receive and hold the carrier material including the antibiotics. A suitable carrier material is for instance a cement such as used in connection with the implantation of protheses or the like sofar it allows the protracted release of the antibiotics.

Advantageous embodiments and further developments of this fundamental concept are illustrated in the sub-claims; in particular, it should be pointed out that it is, of course, possible to machine the surface of the aid for osteosynthesis, and the receiving spaces or surfaces formed in or on this aid, so that, by this means, the adhesion between the aid for osteosynthesis and the carrier material for the antibiotic is improved.

According to a further essential characteristic of the invention, it is furthermore proposed that the outside of the actual carrier material can also be roughened in order thus to ensure better fixation by new formation of bone at the surface of the implant. This measure is particularly important in the case of implants, for example in artificial joints.

In a further embodiment of the concept according to the invention the procedure is such that the area, of the aid for osteosynthesis, which may have to be bent is left free from carrier material from the start, so that problem-free bending of the aid is possible. Subsequently, this area, like the screws or the like which, for example, are used, can then be covered with additional carrier materials, small plates or caps.

To summarise, it can be stated that by means of the proposal according to the invention an exceptionally high release of active ingredient in the immediate area of the fracture or of the operated area is ensured in every case.

BRIEF DESCRIPTION OF THE DRAWING

An illustrative embodiment of the invention is shown in the appended drawing. The drawing shows in FIG. 1 is a diagrammatic representation of a slightly domed bone plate of the type which nowadays is part of the prior art, in FIG. 2 is a modified embodiment according to FIG. 1, processed in accordance with a proposal according to the invention, in FIG. 3 an aid, for osteosynthesis, according to FIG. 2 with inserted antibiotic, in FIG. 4 a section along line 4—4 in FIG. 1, in FIG. 5 a section along line 5—5 in FIG. 2, and in FIG. 6 a section along line 6—6 in FIG. 3.

DETAILED DESCRIPTION OF THE PREFERRED EMBODIMENTS

Figure 1:
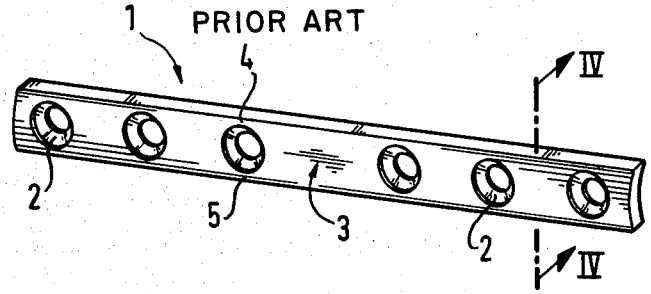
Figure 4:
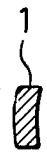

FIGS. 1 and 4 show a slightly domed bone plate which is given the general designation 1 and in which spaces 2 for the screws used to fix the plate to the bone or to the opposite plate are provided.

In the illustrative embodiment according to FIG. 1, which is shown, a screw-free region 3, which bridges the fracture, is provided in the central region of the plate 1.

It can be seen that the tensile strength and flexural strength obtained with this plate 1 are determined by the regions 4 and 5 which are located laterally alongside the bore 2 for receiving a screw, since these are the regions where the amount of material is smallest.

Figure 2:
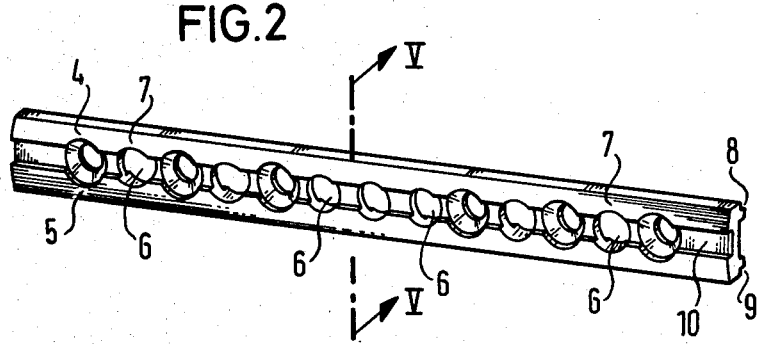

On the basis of this consideration it is now proposed, according to the invention, to machine the blank of a plate 1, shown in FIG. 1, in accordance with the representation in FIG. 2, that is to say additional bores 6, which serve as receiving spaces, are introduced, but these do not impair the flexural strength of the plate since an edge designated 7 in FIG. 2 is left on the outside of these bores and this edge has at least the same strength as the regions 4 and 5.

Figure 5:
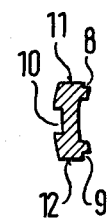

Moreover, as can be seen from the section along line 5—5 shown in FIG. 5, this plate can be provided with additional milled recesses 8 and 9 and 10. These milled recesses 8 to 10, like the bores 6, serve to receive a carrier material 14 which carries the antibiotic.

Figure 3:
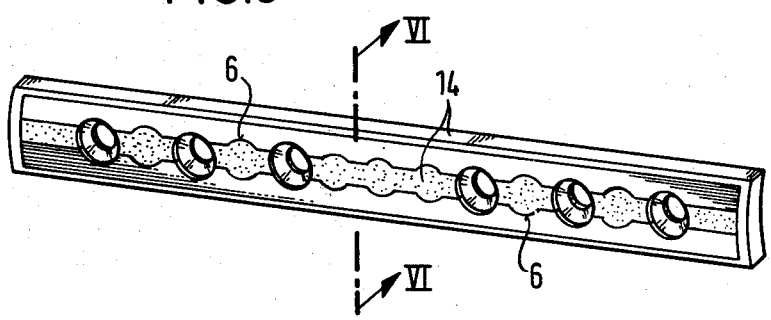
Figure 6:

Finally, FIG. 3 shows the aid, for osteosynthesis, according to FIG. 2—but now provided with the carrier material 14—and it can be seen that this carrier material 14 is not only located in the abovementioned recesses 8 to 10 and the bore 6 but additionally can also be deposited on the outer edges 11 and 12, so that it is thus possible to provide for combining a large amount of carrier material 14 with the actual aid, for osteosynthesis, which is made of metal in the illustrative examples shown, by which means, at the same time, a relatively large amount of antibiotics can be applied to the focus of infection. Due to the protracted release of this antibiotic, a long-term treatment is now possible, but at the same time no spatial change in the aid for osteosynthesis occurs as a result of the release of the antibiotic.

At the same time, when the aid for osteosynthesis is removed the carrier material is also removed, so that both the antibiotic and the aid for osteosynthesis can be removed in a single operation.

Whilst in the illustrative embodiment shown in FIG. 1 a region 3 which is without holes or screws is provided, in the arrangement, according to the invention, according to FIGS. 2 and 3 this region is also provided with receiving spaces 6, which are intended to receive the carrier material.

The possibility for roughening the outside of the carrier material is shown in FIG. 3. This measure is particularly meaningful if an artificial joint or similar implant is to be furnished in accordance with the proposal of the invention, in which case a considerably better fixation due to new formation of bone at the surface of the aid is ensured as a result of this roughening, since the critical metal/cancellous tissue boundary surface is circumvented. Thus, with this latter proposal good growing-in and good tolerance of the implanted aid is achieved at the same time, in combination with a high release of active ingredient in the decisive area.

I claim:

1. An aid removably appliable to a bone at an osteosynthesis site to assist in fusing the bone, said aid comprising:

an elongated, bar like member for bridging the osteosynthesis site, said member being formed of a material having sufficient strength to provide the necessary stabilizing assistance to the bone, said member having perforations for receiving fasteners removably applying the member to the bone, and said member having at least one indentation in the surface thereof; and a carrier material fixed in said indentation of said member, said material being non-absorbable by body tissue and of constant surface form and integrity, said material having an antibiotic substance uniformly distributed therein and released therefrom at a controlled rate.

2. An aid for osteosynthesis according to claim 1 characterized in that the indentation is provided with a configuration which increases the fixing of the carrier material to the member.

3. An aid for osteosynthesis according to claim 1, characterized in that the outside of the carrier material (14) is roughened.

4. An aid according to claim 1 characterized in that the member is so formed that the material receiving indentation is provided therein while the desired strength and external shape of the member is maintained.

5. The aid according to claim 1 wherein said indentation is so located in said member as to provide a carrier material-free area in said member permitting the bending of said member.

6. An aid for osteosynthesis according to claim 5, characterized by caps covering the carrier material-free areas of said member.

7. The aid according to claim 1 wherein said indentation comprises at least one additional perforation in said member.

8. The aid according to claim 1 wherein said indentation comprises at least one groove in said member.

9. The aid according to claim 1 wherein said material is so formed as to present an exterior surface flush with the surface of said member surrounding said indentation.

* * * * *